(12) United States Patent
Dillenback

(10) Patent No.: US 6,553,777 B2
(45) Date of Patent: Apr. 29, 2003

(54) CENTRAL MEDIA DISPENSER FOR USE IN HVAC SYSTEM

(76) Inventor: Scott J. Dillenback, 100 Briarwood Ct., New Hartford, NY (US) 13413

( * ) Notice: Subject to any disclaimer, the term of this patent is extended or adjusted under 35 U.S.C. 154(b) by 0 days.

(21) Appl. No.: 09/796,177

(22) Filed: Feb. 28, 2001

(65) Prior Publication Data

US 2002/0116937 A1 Aug. 29, 2002

(51) Int. Cl.[7] .............................. F28D 3/00; F24F 3/16; F24F 3/14; F28C 1/00; F25D 17/00; F25B 41/00
(52) U.S. Cl. .............................. 62/171; 62/78; 62/121; 62/179; 62/208; 126/113; 222/1; 261/DIG. 17
(58) Field of Search .................... 126/113; 137/268; 222/1; 261/DIG. 17; 62/171, 179, 78, 208, 207, 121

(56) References Cited

U.S. PATENT DOCUMENTS

| | | | |
|---|---|---|---|
| 3,140,147 A | 7/1964 | Neuwald | |
| 3,178,255 A | 4/1965 | Neuwald | |
| 3,510,252 A | 5/1970 | Reich | |
| 4,229,415 A | 10/1980 | Bryson | |
| 4,617,157 A | 10/1986 | Stein | |
| 4,742,475 A | * 5/1988 | Kaiser et al. | ................ 165/208 |
| 4,752,422 A | 6/1988 | Uchida | |
| 4,913,034 A | * 4/1990 | Ripple et al. | ................ 126/113 |
| 5,029,729 A | 7/1991 | Madsen | |
| 5,078,046 A | * 1/1992 | Mascolo et al. | ..... 261/DIG. 17 |
| 5,186,869 A | 2/1993 | Stumpf | |
| 5,196,171 A | 3/1993 | Peltier | |
| 5,240,487 A | 8/1993 | Kung | |
| 5,382,410 A | 1/1995 | Peltier | |
| 5,494,644 A | * 2/1996 | Thomas et al. | ............. 137/268 |
| 5,607,651 A | 3/1997 | Thomas | |
| 5,720,176 A | 2/1998 | Manson | |
| 5,724,256 A | 3/1998 | Lee et al. | |
| 5,805,768 A | 9/1998 | Schwartz | |
| 5,924,297 A | 7/1999 | Lynn | |
| 5,924,597 A | * 7/1999 | Lynn | .............................. 222/1 |

* cited by examiner

Primary Examiner—William C. Doerrler
Assistant Examiner—Filip Zec
(74) Attorney, Agent, or Firm—August E. Roehrig, Jr.; Hancock & Estabrook, LLP

(57) ABSTRACT

A user-programmable monitoring and dispensing system for controlling the dispensing of water vapor and various other media into an HVAC air stream in residential or commercial structures. The various media to be dispensed are preferably water-soluble, and mixed with the system water supply to be dispensed with the water vapor added to the HVAC air stream. These materials may be fragrances or aromas, intended to produce an aesthetic effect, or they can be agents capable of pesticidal, bacteriacidal, fungicidal or sporacidal effect for use as acute or prophylactic treatment for infestation.

34 Claims, 5 Drawing Sheets

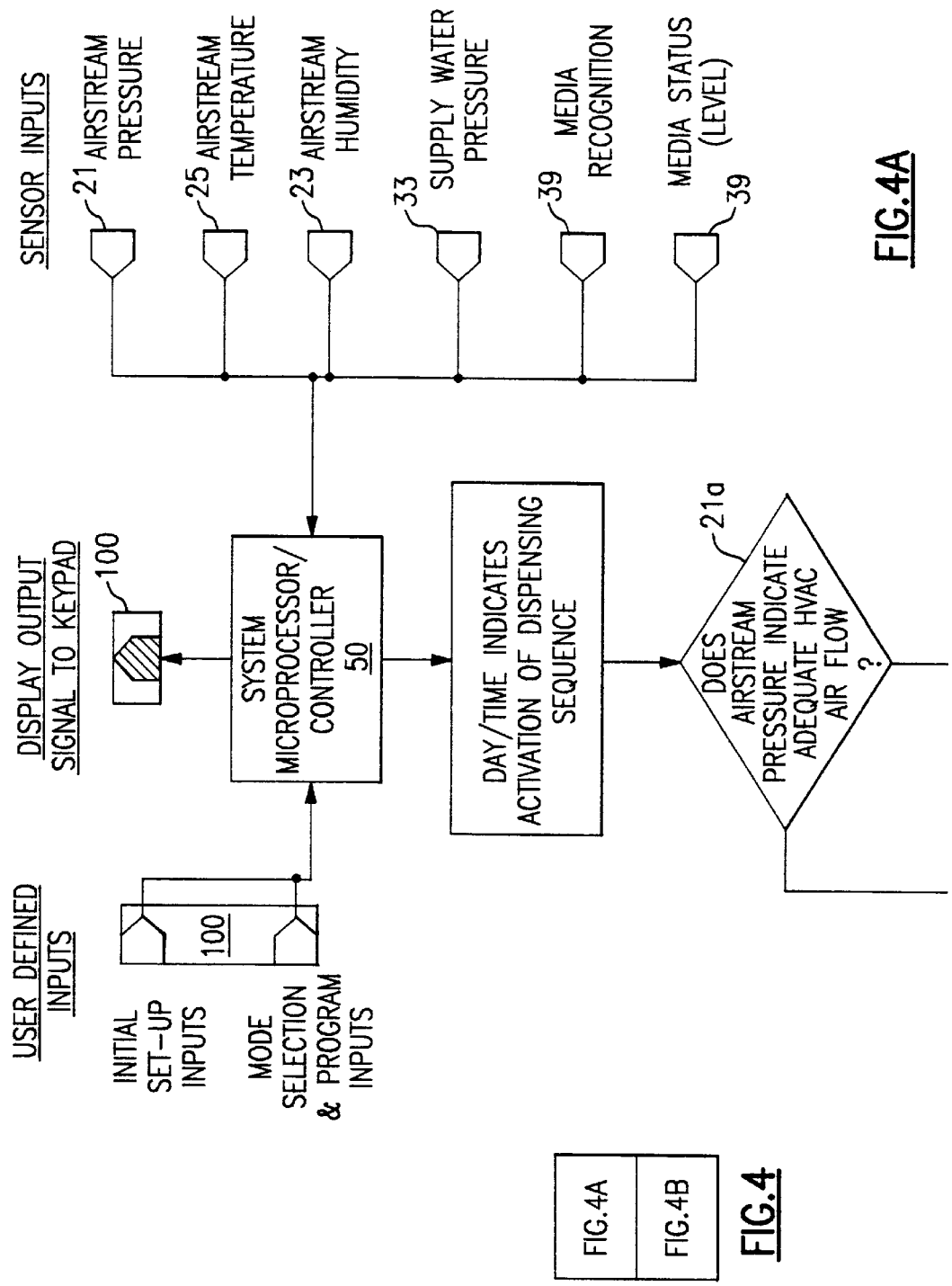

CENTRAL MEDIA DISPENSER FOR USE IN HVAC SYSTEM

BACKGROUND OF THE INVENTION

1. Field of the Invention

This invention relates in general to a dispensing system for use in a heating, ventilating or air conditioning (HVAC) air stream and, in particular, to a central or zoned forced air HVAC media dispensing system for dispensing water vapor and/or other water soluble air-flow borne materials.

More specifically, but without restriction to the particular embodiment and/or use which is shown and described herein for purposes of illustration, this invention relates to a user-programmable central or zoned HVAC dispensing system for introducing various media such as water vapor, fragrances or other air-treating materials to improve living and working environments.

2. Description of Related Technology

The use of a humidification device for a central or zoned forced air HVAC system to improve living and working environments is known to those skilled in this art. Such systems generally comprise either passive evaporation of water from a reservoir adjacent to the HVAC air stream, or a circulating liquid retaining medium which passes in an endless path of movement through a water bath positioned within the HVAC air stream. While such systems are somewhat effective and simple, they are generally activated when an air stream is moving through the HVAC system and do not provide precise user control. If it is desired to dispense an additional medium into the air stream, the additional medium is manually added to the bath for dispensing into the air flow. Such systems consequently have wide variations in the amount of the media dispensed into the air stream which changes as the concentration of the media being dispensed varies, such as by evaporation, as well as the conditions of the ambient air.

SUMMARY OF THE INVENTION

It is therefore an object of this invention to improve central and zoned dispensing systems for dispensing materials into a HVAC air stream.

Another object of this invention is to provide a range of user-programmable operational controls for the dispensing of materials into an HVAC air stream.

A further object of this invention is to provide a user-programmable central dispensing system for dispensing and monitoring the dispensing of one or more water-soluble materials into the air stream of an HVAC system in a predetermined and programmable quantity.

These and other objects are attained in accordance with the present invention wherein there is provided a user-programmable monitoring and dispensing system for controlling the dispensing of water vapor and various other media into an HVAC air stream in residential or commercial structures. The various media to be dispensed are preferably water-soluble, and mixed with the system water supply to be dispensed with the water vapor added to the HVAC air stream. These materials may be fragrances or aromas, intended to produce an aesthetic effect, or they can be agents capable of pesticidal, bacteriacidal, fungicidal or sporacidal effect for use as acute or prophylactic treatment for infestation.

DESCRIPTION OF THE DRAWINGS

Further objects of this invention, together with additional features contributing thereto and advantages accruing therefrom, will be apparent from the following description of a preferred embodiment of the present invention which is shown in the accompanying drawings with like reference numerals indicating corresponding parts throughout and which is to be read in conjunction with the following drawings, wherein.

These and additional embodiments of the invention may now be better understood by referring to the following detailed description of the invention wherein the illustrated embodiment is described.

DETAILED DESCRIPTION OF THE INVENTION

Throughout this description, the preferred embodiment and examples shown should be considered as exemplars, rather than limitations on the apparatus and methods of the present invention.

Figure 1:
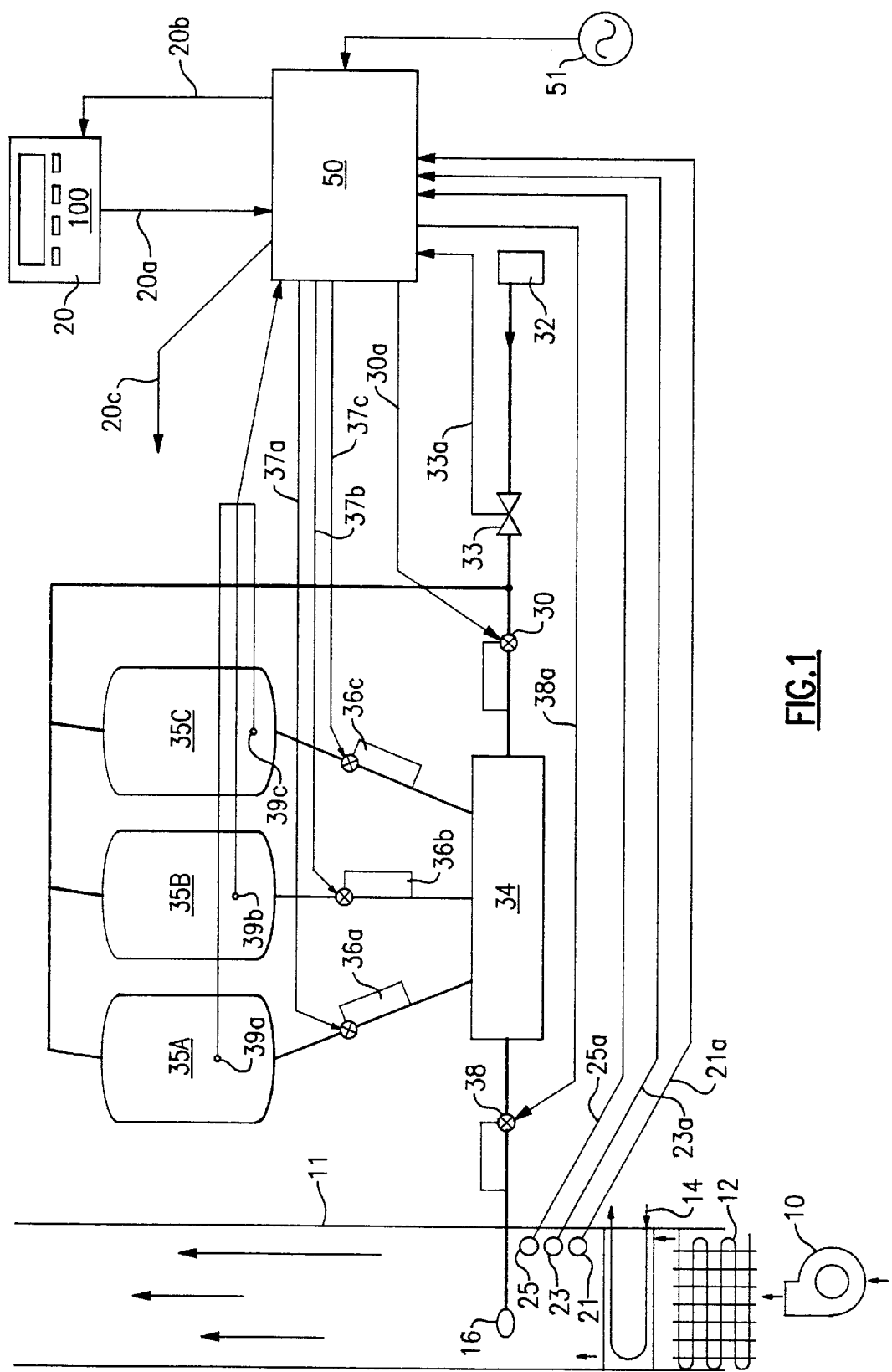
FIG. 1 is a mechanical schematic of a preferred embodiment of the dispensing system to better illustrate the components thereof and the manner in which such components interrelate in the system operation.

Referring now to the drawings, there is illustrated in FIG. 1 the various air flow components of an HVAC system and the central dispensing system of this invention. The portion of the HVAC system illustrated includes an air movement generating device, such as a blower 10 which generates an air stream which pass through duct work 11 to a desired residential or commercial space. The HVAC system includes a heat exchanger 12 positioned in the air stream path to heat the air moving through the duct 11 in response to the temperature set by a HVAC thermostat controller 20, the input of which is entered through a user operated keypad/display unit 100. In addition, an A/C coil 14 is positioned in the air stream to cool the temperature thereof in response to the temperature programmed through the thermostat 20. The blower 10, duct work 11, heat exchanger 12 and A/C coil 14 are standard components utilized in HVAC forced air systems. Positioned down stream from the blower 10, heat exchanger 12 and A/C coil 14, in the direction of air movement, is a pressure or flow sensor 21, such as available from Sensotec Inc., 2080 Arlingate Lane, Columbus, Ohio 43228, a humidity sensor 23 and a temperature sensor 25, such as a HE-6310 Series Duct-mount humidity/temperature sensor, available from Johnson Controls, Inc., 507 East Michigan Street, Milwaukee, Wis. 53202, all of which are connected to a system central processor 50, such as an Intel Type 8051 Microcontroller DS89C420-QCS Dallas Semiconductor Ultra High Speed 8051 Based Microcontroller PLCC Package available from Newark Electronics, 3 Marcus Boulevard, Albany, N.Y. 12205-1129, for providing air stream sensor inputs as to the air movement, moisture content of the air stream and the air stream temperature to the system central processor. Further down stream from these sensors, is a dispenser 16 which may be in the form of an ultrasonic transducer, available from Keramos Advanced Piezoelectrics, 5460 W. 84$^{th}$ Street, Indianapolis, Ind. 46268 and Etalon Innovative Piezo Transducers, P.O. Box 127, Lebanon, Ind. 46052, or vaporizer through which water vapor and/or water-soluble materials, available from Aroma Tech Co., 130 Industrial Parkway, Somerville, N.J. 088076, are dispensed into the HVAC air stream in response to a user-defined program input to the system central processor 50 by means of the keypad/display unit 100, such as a Type XK-5LC or Type LCD-96M Multi Menu Keypad available from FBII, 149 Eileen Way, Soyosset, N.Y. 11791-5316 or JDS Technologies, 12200 Thatcher Ct., Poway, Calif. 92064-6876. While a single dispenser 16 is illustrated, it is to be understood that a single dispensing head may be utilized as illustrated or multiple dispensing heads may be utilized with each one of the multiple dispensing heads being connected by means of a dilution manifold to each individual media reservoir. The dispensing heads may be piezo-electric ultrasonic transducers, atomizer spray nozzles or a media saturated evaporation wick. The dispenser 16, as illustrated in FIG. 1, is shown dispensing into the main plenum of an HVAC system for a centralized effect from the medium dispensed. However, it is to be understood that separate dispensers may be utilized in various trunk ducts as well as the central plenum for dispersal of the medium into specific locations serviced by the HVAC system.

Figure 2:
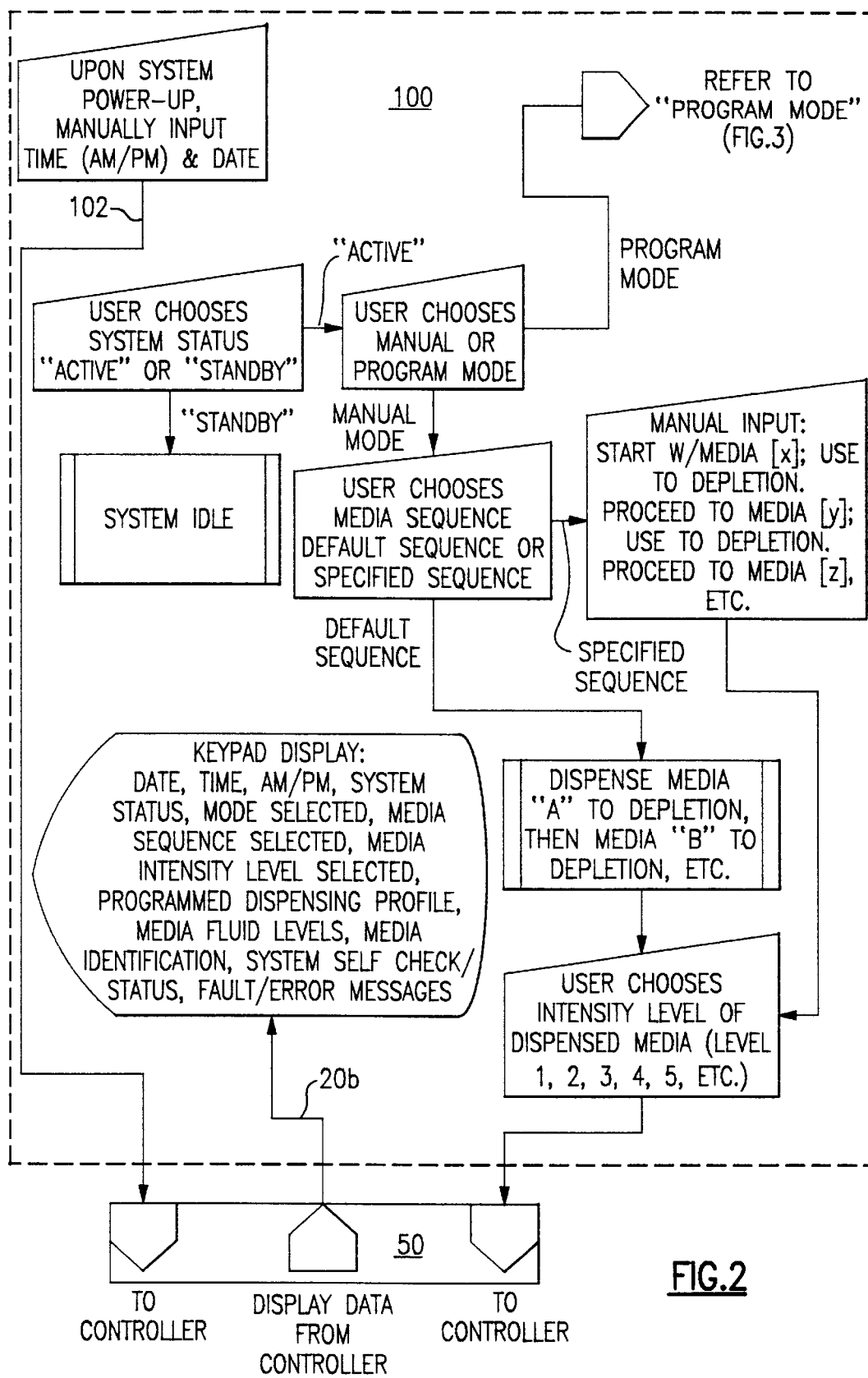
FIG. 2 is a logic block diagram of the system operation.

The display/HVAC thermostat portion 20 of the keypad/display unit 100 is coupled to the system central processor 50 to provide the inputs illustrated in FIG. 2 to control the heating/cooling operation of the system central processor 50.

The system central processor 50 is connected to a suitable standard power supply 51 to provide power to the unit upon start up. At this time a thermostat control signal is sent 20c from the system central processor 50 to actuate one or more of the blower 10, heat exchanger 12, or A/C coil 14, in response to an on/off signal determined from the thermostat setting.

Figure 3:
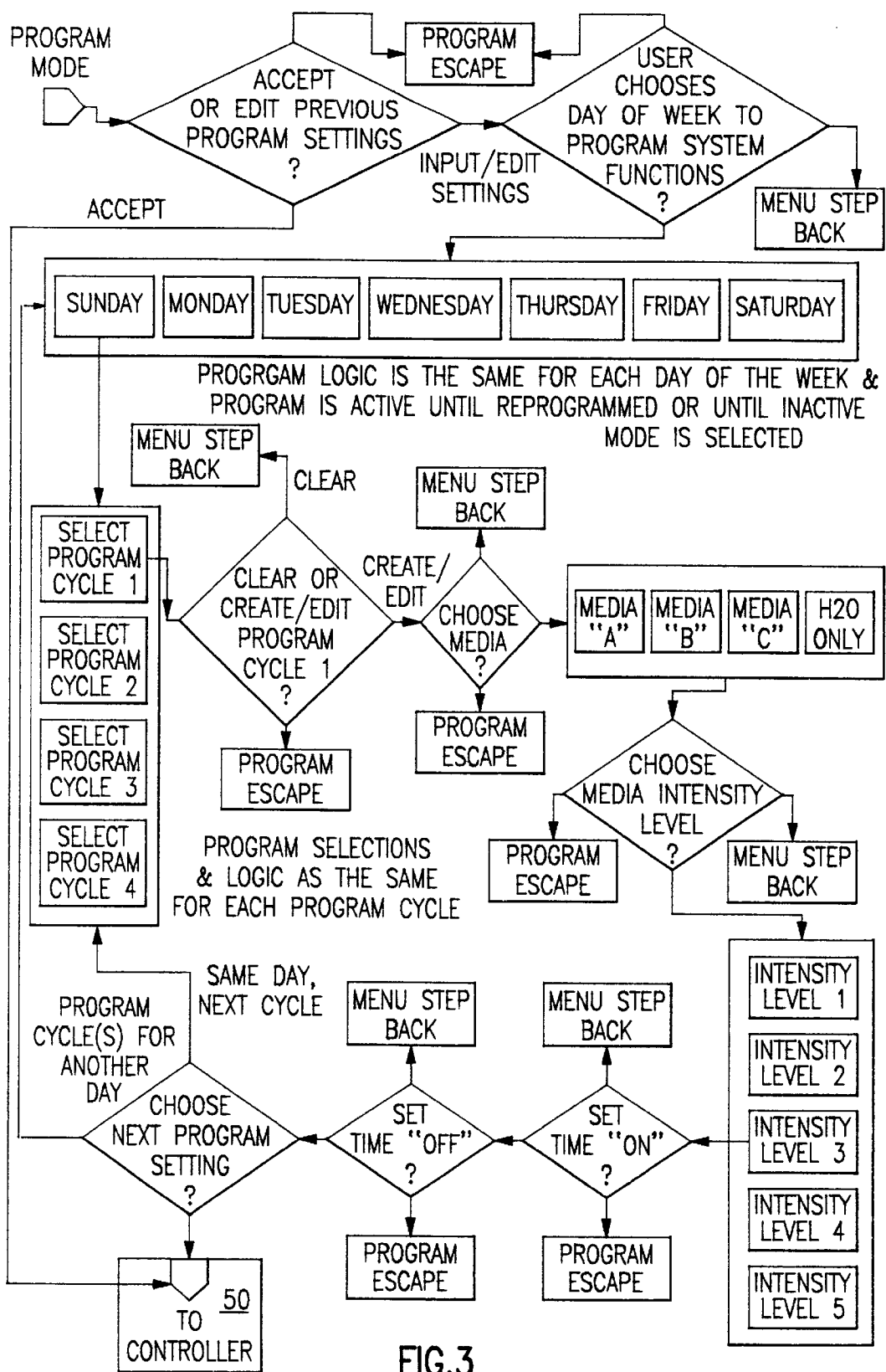
FIG. 3 is a logic block diagram of the operation of the user interface keypad/display through which the system is programmed.

The system central processor 50 is programmed in the manner illustrated in FIG. 3, to control the operation of the media dispensing system on a daily basis, to control the dispensing of a selected medium or media, and to control the intensity thereof during the programmed cycle. The system operation, in response to the user-defined program inputs, and the output from various component sensors used in controlling system operations, are controlled in the manner illustrated in FIG. 4.

Referring again to FIG. 1, the input from the user-defined program keypad/display unit 100, including the thermostat signal, is coupled 20a to the system central processor 50 and appropriate display information is coupled 20b from the system central processor 50 back to the keypad/display 100 to confirm that the signals input from the keypad/display unit 100 have been received and processed by the system central processor 50. While in the preferred embodiment disclosed herein as the best mode contemplated by the inventor for practicing the invention the keypad/display unit 100 is utilized, it is to be understood that the input coupled 20a to the dispenser system central processor 50 could be from a home automation control system commonly used to network and integrate the control and function of several subsystems in the space being controlled, with the feedback 20b from the system central processor 50 being coupled to such an automation control system instead of a keypad/display unit 100. A suitable home automation control system, not shown, has been found to be an Omni, Omni LT, and Omni Pro models available from Home Automation, Inc., 5725 Powell Street, Suite A, New Orleans, La. 70123.

When the HVAC system is in operation, an input 21a will be received from the pressure or flow sensor 21 to the system central processor 50 confirming the movement of the air stream in the duct 11, and input signals will be received 23a from the humidity sensor 23 and from the temperature sensor 25 to provide input 25a to the system central processor 50 as to the moisture content and the temperature of the air stream moving through the duct 11. This information will be processed through the system central processor 50 and control 30a the operation of a water intake control valve 30, available from South Bend Controls, 1237 Northside Boulevard, South Bend, Ind. 46615; HydraForce, Inc., 500 Barclay Boulevard, Lincolnshire, Ill. 60069; and Deltrol Controls, 2740 South $20^{th}$ Street, Milwaukee, Wis. 53215, through which water passes from a suitable municipal or domestic supply source 32 into a dilution manifold 34 wherein water soluble media to be dispensed into the air stream are added for dilution prior to dispensing.

The water from water supply 32 is also connected to one or more media reservoir tanks, illustrated in the preferred embodiment as three reservoirs 35a, 35b and 35c. These reservoirs may be either permanent containers which are refillable, or be replaceable as modular units. In addition, each reservoir 35a, 35b and 35c incorporates a recognition media such as a bar code, magnetic strip or holographic symbol so that the system central processor 50 will receive a signal that the reservoir is in proper position and the information contained therein will effect display of the particular medium being dispensed on the keypad/display unit 100. In addition, it is to be understood that the contour of each of the reservoirs may be such that when the reservoir is properly positioned, such a signal will be provided to the system central processor.

Each of the reservoirs 35a, 35b and 35c preferably contain an inner bladder which effectively creates a second chamber within the media reservoir and the space around the inner bladder is connected in parallel to the water supply 32 such that the water fills the space around the bladder to displace the media contained within the reservoir towards the mixing manifold. Each of the media reservoirs is connected to the dilution manifold 34 by media output valves 36a, 36b and 36c such as inert proportional valves available from the water intake control valve supplier and which are individually activated 37a, 37b and 37c by the system control processor 50 to control the dispensing of water soluble media into the dilution manifold 34 from the respective media reservoirs 35a, 35b and 35c. The water soluble media is mixed with water in the dilution manifold 34 and passes to the ultrasonic transducer or vaporizer 16 in response to the actuation 38a of a dispensing control valve 38 available from the water intake control valve suppliers previously identified and operated by the system central processor 50 in accordance with the information coupled to the central system processor by the temperature and humidity sensors 25 and 23, respectively, and the programmed input entered by the user through the keypad/display unit 100. The intensity of the media contained within the media reservoirs may be achieved by varying the amount of media dispensed during and "on" cycle wherein the media reservoirs contain a constant concentration of the media or the quantity of the medium dispensed may be held constant with the concentration of the media being controlled by controlling the dilution of the medium in the dilution manifold 34.

The media reservoirs 35a, 35b and 35c are each provided with a sensor 39a, 39b and 39c, respectively, available from Gems Sensors, 1 Cowles Road, Plainville, Conn. 06062, coupled to the system central processor 50 to monitor the level of the medium contained within each reservoir for proper dispensing of the medium contained therein. Alternatively, instead of actively monitoring the level of the medium in the reservoirs 35a, 35b and 35c, the system central processor 50 could calculate the quantity dispensed and thereby derive the amount remaining, assuming that the initial amount supplied to these reservoirs is constant, or otherwise "known" by the system central processor. The system central processor 50 can be programmed, as illustrated in FIG. 3, to dispense one or more of the media from the reservoirs 35a, 35b and 35c into the dilution manifold 34 in increments stepped to vary the intensity or concentration of the media in the dilution manifold in accordance with the input to the system central processor 50 through the keypad/display unit 100. A water supply pressure feedback input 33a is connected to the system control processor 50 from a check valve and pressure sensor 33, available from Sensotec Inc. 2080 Arlingate Lane, Columbus, Ohio 43228, carried in the municipal or domestic water supply line to ensure that an adequate supply of domestic water 32 at a desired pressure is available for use in the dispensing system.

Referring now to FIG. 2, there is illustrated the informational inputs that a user enters into the system through operation of the keypad/display unit 100 to control operation of the system central processor 50 to perform the desired functions. Upon initial system power-up, the user manually enters the time and date through the keypad/display unit 100 which is coupled 102 to the system central processor 50. This information, once coupled to the system central processor 50, will be used by the processor to accurately maintain current time in a manner known to those skilled in the art, and displayed on the keypad/display unit 100.

The user then enters information to place the system central processor in either an "Active" or "Standby" mode. If the "Standby" mode is selected, the system central processor 100 will be idle and the keypad/display unit 100 will display that the system is in the "Standby" mode awaiting further instruction. If the user elects to operate the system, the "Active" mode is selected, displayed, and the user may elect to have the system operated in either a "Manual" or "Program" mode. If the "Manual" mode of operation is selected, the user can either elect to have the system operate in a "Default" sequence or a "Specified" sequence of operation.

In the "Default" sequence of operation, the system central processor 50 will sequentially actuate the first medium dispenser 35a which will continue to operate to depletion. Upon depletion a signal will be sent by the sensor 39a to the system central processor 50 which will then actuate the next available medium dispenser, e.g.: 35b, which will continue to operate to depletion. At that time the sensor 39b will send a signal to the system central processor 50 which will actuate the next available medium dispenser until all of the medium has been dispensed, at which time the system central processor 50 will cause a message to be displayed on the keypad/display unit 100 that the dispensers are empty and the system has been placed on "Standby".

If the user elects to choose a "Specified" sequence rather than the "Default" sequence, the user can input a particular order by which the media will be used to depletion, by entering instructions through the keypad/display unit 100 for the system central processor 50 to start with a first programmed medium dispenser and then proceed upon depletion to a second specified medium dispenser and upon the depletion thereof to proceed to another specified medium dispenser. However, regardless of which mode of operation the user selects, in either of these modes the user is required to set the intensity level of each of the media to be discharged from the dispenser 35a, 35b, and 35c into the dilution manifold 34. The manner in which the intensity parameters are input to the system central processor 50 is illustrated in FIG. 3.

If the user chooses to operate the system in a "Program" mode, whereby individual medium and intensity parameters can be selected and set for individual days of the week, the user selects the "Program" option when the system "Active" display is presented.

Referring to FIG. 3, upon entering the "Program" mode the user is instructed to either accept or edit a previous program setting. If at this time the user elects not to enter the "Program" mode, an "Escape" instruction is provided which returns the user to the "Active" display whereby the system may be operated in the "Manual" mode or the user may return the system to the "Standby" mode. If, however, the user elects to proceed with the "Program" mode, the user must either "Accept" the previous program settings (or the factory settings if this is an initial installation) or select the "Edit" option if it is desired to make changes in the program previously entered. Throughout the operation in the "Program" mode, an "Escape" option is available to enable the user to return to the "Active" input level thereby cancelling all instructions entered to that point and the system returning to the previous program settings, or a "Menu Step Back" option is also available to permit the user to correct an entry error without losing the settings previously entered.

Upon selecting the "Edit" option, the user sequentially selects each day of the week to define the parameters of operation of the system for that day. These parameters include the time of program operation, identified as "Cycle 1", "Cycle 2", "Cycle 3" and "Cycle 4". These times of operation are set for each day and may be individually accepted as presented previously, or edited. After the program cycle is selected, the particular medium, water vapor only or one of the media 35a, 35b, 35c which is to be dispensed, may be chosen. The intensity level (concentration) of the selected medium which is to be dispensed may be selected as well as the time period selected for operation during the program cycle can be chosen and entered through the keyboard/display unit 100 into the system central processor 50. This information is sequentially entered into the system central processor 50 through the keypad/display unit 100 for each day of the week.

Functional Description

Figure 4B:
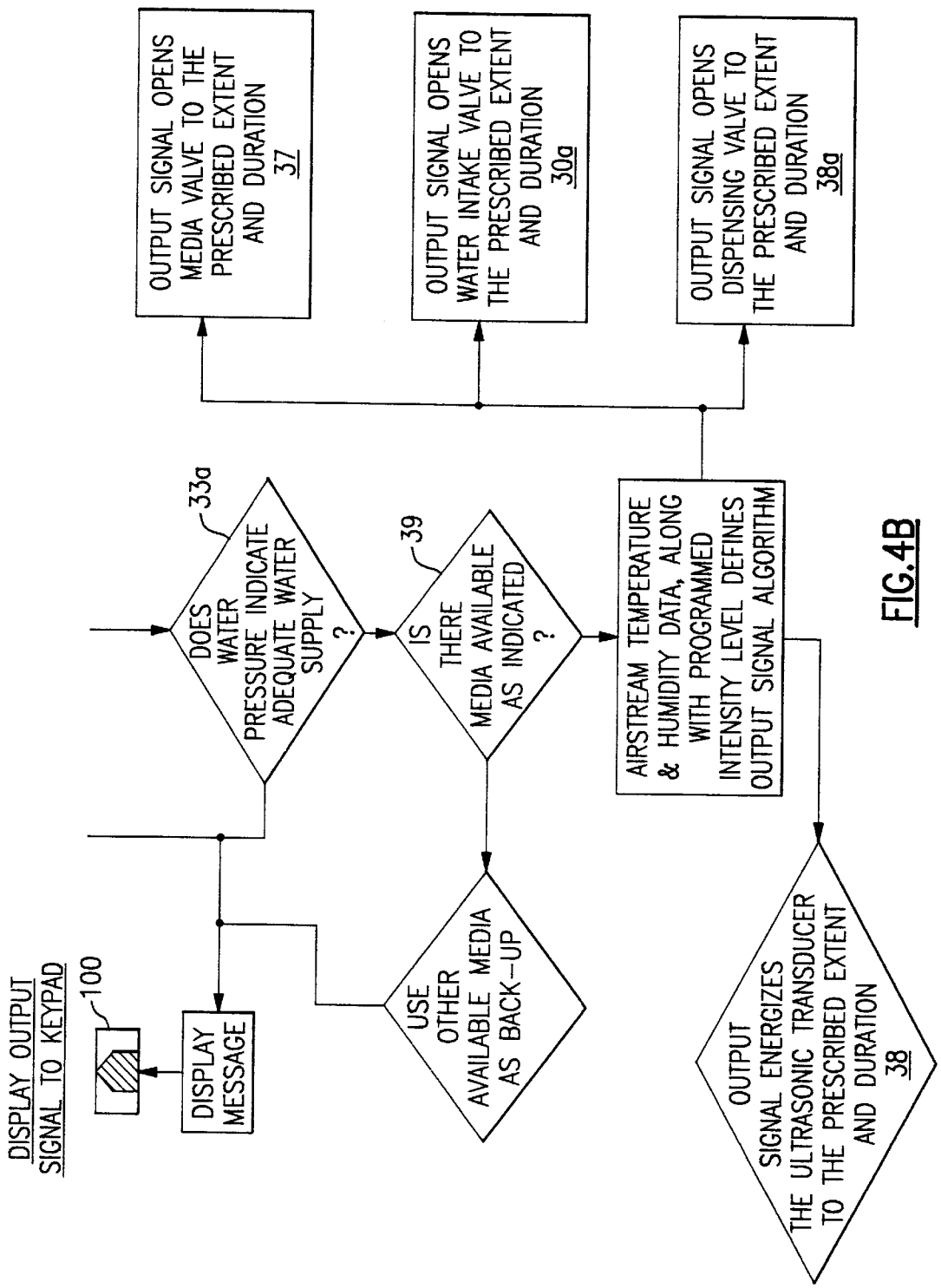
FIG. 4 is a logic block diagram of the system controls through which materials are dispensed into the HVAC air stream in response to the user-defined program inputs.

Referring now to FIG. 4, the user inputs the initial information into the system central processor 50 through the keypad/display unit 100 in the manner previously described, selects the mode of operation and programs the system as desired. The temperature sensor 25, humidity sensor 23, flow sensor 21, media sensors 39a, 39b, and 39c, and water supply sensor 33a all provide their respective input signals to the system central processor 50. The keyboard/display 100 shows the status of the informational inputs. If the program cycle inputs, the operational sensor inputs and time of operation call for an activation of a dispensing sequence, dispensing operation is initiated and the keypad/display 100 shows that the system is dispensing as instructed. The selected media dispensing valve 36*a*, 36*b* or 36*c* is opened the prescribed extent and duration. The water intake control valve 30 is opened allowing water and the selected medium to mix in the dilution manifold 34. The dispensing control valve 38 is opened and the dispenser 16 is actuated for a time period determined by the parameters of the ambient air moving through the air duct 11. The input from the ambient air flow sensors 21, 23 and 25 coupled to the system central processor 50 prevent the system from dispensing media at a level beyond the capacity of the air stream flow to move the dispensed medium through the HVAC system.

While this invention has been described in the specification and illustrated in the drawings with reference to a preferred embodiment, the structure of which has been disclosed herein, it will be understood by those skilled in the art to which this invention pertains that various changes may be made, and equivalents may be substituted for elements of the invention without departing from the scope of the claims. Therefore, it is intended that the invention not be limited to the particular embodiment disclosed in the specification and shown in the drawings as the best mode presently known by the inventors for carrying out this invention, nor confined to the details set forth, but that the invention will include all embodiments, modifications and changes as may come within the scope of the following claims:

What is claimed is:

1. A user-programmable media dispensing system for use in a central or zoned forced-air heating, ventilating and air-conditioning system comprising:

dispensing means actuable in response to a dispenser activating control signal to discharge a quantity of a medium into an air stream of a central or zoned forced-air heating, ventilating and air-conditioning system;

a dispensing system central processor coupled to said dispensing means and generating a dispenser activating control signal to said dispensing means in response to instruction input signals coupled to said dispensing system central processor from user-programmable data entry;

said dispensing means including a plurality of dispensing media containing reservoirs coupled in fluid communication with a media dispenser;

said media dispenser being positioned in the air stream of a central or zoned forced-air heating, ventilating and air-conditioning system for dispensing the media contained in at least one of said dispensing media containing reservoirs into said air stream in response to said dispenser activating control signal generated by said dispenser system central processor;

each one of said plurality of dispensing media containing reservoirs including a media output discharge control valve coupled in fluid communication between said dispensing media containing reservoir and said media dispenser for receiving said dispenser activating control signal generated by said dispenser system central processor to selectively control the discharge of dispensing media therethrough;

user-programmable data entry coupled to said dispensing system central processor for entry of user-generated instructions and coupling said user-generated instructions as instruction input signals to said dispensing system central processor for generating said dispenser activating control signals to actuate said dispensing means;

air stream sensor means positioned in the air stream of a central or zoned forced-air heating, ventilating and air-conditioning system and coupled to said dispensing system central processor for generating ambient-air-determined control signals to said dispensing system central processor to control the generation of said dispenser activating control signals to actuate said dispensing means; and a dilution manifold in fluid communication with said media dispenser and each one of said media output discharge control valves to receive and dilute the dispensing media discharged through said output discharge control valves prior to passing to said media dispenser.

2. The media dispensing system of claim 1 further including a source of pressurized water coupled to said dilution manifold for diluting the concentration of said dispensing media discharged into said discharge manifold through said media output discharge control valves prior to passing to said media dispenser.

3. The media dispensing system of claim 2 further including a water intake control valve in fluid communication with said dilution manifold and said source of pressurized water, said water intake control valve operable in response to an activating signal from said dispensing system central processor for discharging into said dilution manifold.

4. The media dispensing system of claim 3 wherein said source of pressurized water coupled to said dilution manifold includes a check valve and pressure sensor, said pressure sensor being coupled to said dispensing system central processor for providing a control signal thereto in response to said water pressure input.

5. The media dispensing system of claim 1 wherein said air stream sensor means includes at least one of:

a temperature sensor for generating a control signal responsive to the air stream temperature, a humidity sensor for generating a control signal responsive to the air stream relative humidity, or an air pressure/air flow sensor for generating a control signal responsive to the air stream air pressure/air flow.

6. The media dispensing system of claim 1 wherein each one of said plurality of dispensing media containing reservoirs includes a media reservoir sensor coupled to said dispensing system central processor for generating a signal thereto responsive to the amount of media contained therein.

7. A user-programmable media dispensing system for use in a central or zoned forced-air heating, ventilating and air-conditioning system comprising:

dispensing means actuable in response to a dispenser activating control signal to discharge a quantity of a medium into an air stream of a central or zoned forced-air heating, ventilating and air-conditioning system;

a dispensing system central processor coupled to said dispensing means and generating a dispenser activating control signal to said dispensing means in response to instruction input signals coupled to said dispensing system central processor from user-programmable data entry;

said dispensing means including a plurality of dispensing media containing reservoirs coupled in fluid communication with a media dispenser;

said media dispenser being positioned in the air stream of a central or zoned forced-air heating, ventilating and air-conditioning system for dispensing the media contained in at least one of said dispensing media containing reservoirs into said air stream in response to said dispenser activating control signal generated by said dispenser system central processor;

each one of said plurality of dispensing media containing reservoirs includes a media reservoir sensor coupled to said dispensing system central processor for generating a signal thereto responsive to the amount of media contained therein;

user-programmable data entry coupled to said dispensing system central processor for entry of user-generated instructions and coupling said user-generated instructions as instruction input signals to said dispensing system central processor for generating said dispenser activating control signals to actuate said dispensing means;

air stream sensor means positioned in the air stream of a central or zoned forced-air heating, ventilating and air-conditioning system and coupled to said dispensing system central processor for generating ambient-air-determined control signals to said dispensing system central processor to control the generation of said dispenser activating control signals to actuate said dispensing means; and each of said media reservoir sensors generating a signal to said dispensing system control processor responsive to the presence of said media contain reservoir in the dispensing system and the identity of the particular medium contained therein.

8. The media dispensing system of claim 1 wherein said user-programmable data entry keypad-display couples user-generated instruction input signals to said dispensing system central processor to control and display the temperature at said keypad-display.

9. The media dispensing system of claim 1 wherein said user-programmable data entry keypad/display couples user-generated instruction input signals to said dispensing system central processor to control the generation of said dispenser activating control signal by said dispensing system central processor.

10. The media dispensing system of claim 1 wherein said user-programmable data entry keypad-display couples user-generated instruction input signals to said dispensing system central processor to control the generation of said dispenser activating control signal by said dispensing system central processor.

11. The media dispensing system of claim 1 wherein said user-programmable data entry keypad/display couples user-generated instruction input signals to said dispensing system central processor to control the day upon which said dispenser activating signal will be generated by said dispensing system central processor.

12. The media dispensing system of claim 1 wherein said user-programmable data entry keypad/display couples user-generated instruction input signals to said dispensing system central processor to control the day upon which said dispenser activating signal will be generated by said dispensing system central processor.

13. The media dispensing system of claim 1 wherein said user-programmable data entry keypad/display couples user-generated instruction input signals to said dispensing system central processor to control the time at which said dispenser activating signal will be generated by said dispensing system central processor.

14. The media dispensing system of claim 1 wherein said user-programmable data entry keypad/display couples user-generated instruction input signals to said dispensing system central processor to control the time at which said dispenser activating signal will be generated by said dispensing system central processor.

15. The media dispensing system of claim 1 wherein said user-programmable data entry keypad/display couples user-generated instruction input signals to said dispensing system central processor to control the intensity of the medium dispensed by said dispensing means.

16. The media dispensing system of claim 1 wherein said user-programmable data entry keypad/display couples user-generated instruction input signals to said dispensing system central processor to control the intensity of the medium dispensed by said dispensing means.

17. The media dispensing system of claim 1 wherein said user-programmable data entry keypad/display couples user-generated instruction input signals to said dispensing system central processor to control the sequence of dispensing from said plurality of dispensing media containing reservoirs.

18. The media dispensing system of claim 1 wherein said user-programmable data entry is a keypad/display unit.

19. The media dispensing system of claim 1 wherein said user-programmable data entry is an automation control system.

20. The media dispensing system of claim 7 further including a source of pressurized water coupled to said dilution manifold for diluting the concentration of said dispensing media discharged into said discharge manifold through said media output discharge control valves prior to passing to said media dispenser.

21. The media dispensing system of claim 20 further including a water intake control valve in fluid communication with said dilution manifold and said source of pressurized water, said water intake control valve operable in response to an activating signal from said dispensing system central processor for discharging into said dilution manifold.

22. The media dispensing system of claim 21 wherein said source of pressurized water coupled to said dilution manifold includes a check valve and pressure sensor, said pressure sensor being coupled to said dispensing system central processor for providing a control signal thereto in response to said water pressure input.

23. The media dispensing system of claim 7 wherein said user-programmable data entry keypad-display couples user-generated instruction input signals to said dispensing system central processor to control and display the temperature at said keypad-display.

24. The media dispensing system of claim 7 wherein said user-programmable data entry keypad/display couples user-generated instruction input signals to said dispensing system central processor to control the generation of said dispenser activating control signal by said dispensing system central processor.

25. The media dispensing system of claim 7 wherein said user-programmable data entry keypad-display couples user-generated instruction input signals to said dispensing system central processor to control the generation of said dispenser activating control signal by said dispensing system central processor.

26. The media dispensing system of claim 7 wherein said user-programmable data entry keypad/display couples user-generated instruction input signals to said dispensing system central processor to control the day upon which said dispenser activating signal will be generated by said dispensing system central processor.

27. The media dispensing system of claim 7 wherein said user-programmable data entry keypad/display couples user-generated instruction input signals to said dispensing system central processor to control the day upon which said dispenser activating signal will be generated by said dispensing system central processor.

28. The media dispensing system of claim 7 wherein said user-programmable data entry keypad/display couples user-generated instruction input signals to said dispensing system central processor to control the time at which said dispenser activating signal will be generated by said dispensing system central processor.

29. The media dispensing system of claim 7 wherein said user-programmable data entry keypad/display couples user-generated instruction input signals to said dispensing system central processor to control the time at which said dispenser activating signal will be generated by said dispensing system central processor.

30. The media dispensing system of claim 7 wherein said user-programmable data entry keypad/display couples user-generated instruction input signals to said dispensing system central processor to control the intensity of the medium dispensed by said dispensing means.

31. The media dispensing system of claim 7 wherein said user-programmable data entry keypad/display couples user-generated instruction input signals to said dispensing system central processor to control the intensity of the medium dispensed by said dispensing means.

32. The media dispensing system claim 7 wherein said user-programmable data entry keypad/display couples user-generated instruction input signals to said dispensing system central processor to control the sequence of dispensing from said plurality of dispensing media containing reservoirs.

33. The media dispensing system of claim 7 wherein said user-programmable data entry is a keypad/display unit.

34. The media dispensing system of claim 7 wherein said user-programmable data entry is an automation control system.

* * * * *